US010342556B2

(12) United States Patent
Nishio et al.

(10) Patent No.: US 10,342,556 B2
(45) Date of Patent: Jul. 9, 2019

(54) BALLOON WITH DIFFERENT COMPRESSION PORTIONS

(71) Applicant: TERUMO KABUSHIKI KAISHA, Shibuya-ku, Tokyo (JP)

(72) Inventors: Kosuke Nishio, Machida (JP); Riyaheh S. Hazama, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 676 days.

(21) Appl. No.: 14/861,528

(22) Filed: Sep. 22, 2015

(65) Prior Publication Data

US 2016/0089169 A1 Mar. 31, 2016

(30) Foreign Application Priority Data

Sep. 29, 2014 (JP) ................................. 2014-199220

(51) Int. Cl.
| | |
|---|---|
| *A61B 17/22* | (2006.01) |
| *A61M 25/10* | (2013.01) |
| *A61M 29/02* | (2006.01) |
| *A61M 27/00* | (2006.01) |
| *A61F 2/04* | (2013.01) |

(52) U.S. Cl.
CPC ......... *A61B 17/22* (2013.01); *A61M 25/1002* (2013.01); *A61M 29/02* (2013.01); *A61B 2017/22062* (2013.01); *A61F 2002/047* (2013.01); *A61M 25/10184* (2013.11); *A61M 27/00* (2013.01); *A61M 2025/105* (2013.01); *A61M 2025/1075* (2013.01); *A61M 2025/1084* (2013.01); *A61M 2025/1093* (2013.01)

(58) Field of Classification Search
CPC ..... A61M 2025/105; A61M 2025/1075; A61F 2/04; A61B 17/22
See application file for complete search history.

(56) References Cited

U.S. PATENT DOCUMENTS

| | | | | |
|---|---|---|---|---|
| 2008/0188805 | A1* | 8/2008 | Davies | A61M 25/104 604/103.06 |
| 2013/0018448 | A1* | 1/2013 | Folan | A61F 2/958 623/1.11 |
| 2015/0045826 | A1* | 2/2015 | Drasler | A61M 25/104 606/194 |

FOREIGN PATENT DOCUMENTS

JP      2014-057793 A     4/2014

* cited by examiner

*Primary Examiner* — Julie A Szpira
(74) *Attorney, Agent, or Firm* — Buchanan Ingersoll & Rooney PC

(57) ABSTRACT

A balloon including an outer circumferential portion which dilates to form a hollow circular cross-section and deflates when the internal pressure is reduced, an inner circumferential portion positioned inside the outer circumferential portion, and support portions positioned between the outer circumferential portion and the inner circumferential portion to support deflating the outer circumferential portion while compressing the outer circumferential portion. The support portions form first compression portions, which have a high compressive strain, and second compression portions, which have a compressive strain lower than the first compression portions. When the outer circumferential portion deflates, the distance between the center of the circular cross-section and the maximum outer diameter portion becomes shorter than the radius of the circular cross-section formed when a minimum pressure, which is necessary for dilating the outer circumferential portion to have a circular cross-section, is applied to the outer circumferential portion.

8 Claims, 15 Drawing Sheets

BALLOON WITH DIFFERENT COMPRESSION PORTIONS

CROSS-REFERENCE TO RELATED APPLICATION

This application claims priority to Japanese Patent Application No. 2014199220, filed on Sep. 29, 2014, the entire content of which is incorporated herein by reference

TECHNICAL FIELD

The disclosure herein relates to a balloon.

BACKGROUND DISCUSSION

A stenosed site or an occluded site formed in the lumen of blood vessels, urethra, or the like, may be treated using a balloon. The balloon is inserted into the lumen and dilates at the stenosed site or the occluded site.

After the treatment, the balloon is deflated and removed from the lumen. In order to remove the balloon while suppressing damage caused to the inner wall of the lumen, it is desirable to deflate the balloon as much as possible.

For example, JP-A-2014-57793 suggests a method of deflating the balloon by folding it. According to the document, in the balloon, a plurality of "blade portions" are formed to protrude outwardly in a radial direction, and are separated from each other in a circumferential direction. The balloon is folded so that the portions between the blade portions deflate toward the inside in the radial direction.

However, because the size of the "blade portions" is approximately the same as or larger than the radius of the dilated balloon, the blade portions easily interfere with the lumen and hinder the removal of the balloon.

When the internal pressure of the balloon is reduced without folding the balloon, generally, the balloon is crushed and flattened. The width of the flattened cross-sectional shape in a major axis direction becomes greater than the outer diameter of the circular cross-section of the balloon before deflation.

In a case of a balloon used for pressing and bonding a therapeutic sheet onto the stenosed site of the urethra, the outer diameter of the balloon is designed to be greater than the inner diameter of the urethra because the therapeutic sheet needs to be uniformly bonded and pressed onto the stenosed site. Accordingly, if such a balloon is folded as it is in the related art, or if the internal pressure is simply reduced, the maximum width of the deflated balloon may be greater than the inner diameter of the urethra. In this case, the balloon and the inner wall of the urethra interfere with each other, and this makes it difficult to remove the balloon.

SUMMARY

The balloon disclosed here can be more easily removed from a stenosed site or an occluded site.

The balloon includes: an outer circumferential portion that dilates to form a hollow circular cross-section and deflates when the internal pressure thereof is reduced; an inner circumferential portion that is provided inside the outer circumferential portion; and support portions that are provided between the outer circumferential portion and the inner circumferential portion and support the deflating outer circumferential portion while compressing the outer circumferential portion, in which the support portions form a plurality of first compression portions, which have a high compressive strain, and a plurality of second compression portions, which have a compressive strain lower than that of the first compression portions, in a circumferential direction, and because the outer circumferential portion deflates while compressing the first compression portions and the second compression portions, a distance between the center of the circular cross-section and a maximum outer diameter portion which protrudes most toward the outside in a radial direction becomes shorter than the radius of the circular cross-section formed when a minimum pressure, which is necessary for dilating the outer circumferential portion and making the outer circumferential portion have the circular cross-section, is applied to the outer circumferential portion.

The balloon constituted as above deflates such that the overall size in the circumferential direction becomes smaller than the size of the balloon that is obtained when a minimum pressure, which is necessary for dilating the balloon, is applied and thus the balloon dilates to have a circular cross-section. Accordingly, the balloon and the lumen do not easily interfere with each other, and the balloon is easily removed.

When the inner circumferential portion has a hollow shape and dilates or deflates in the radial direction as the pressure between the outer circumferential portion and the inner circumferential portion increases or decreases, other members can be mounted on the balloon through the inner circumferential portion, and the force of fastening other members to the balloon changes as the inner circumferential portion dilates or deflates. Accordingly, the holding force applied to other members can be regulated.

When the outer circumferential portion deflates in the radial direction when the pressure between the outer circumferential portion and the inner circumferential portion is reduced and becomes smaller than the minimum dilating pressure, and if the inner circumferential portion has a hollow shape and dilates in the radial direction when the pressure between the outer circumferential portion and the inner circumferential portion is reduced and becomes smaller than the minimum dilating pressure, when the outer circumferential portion is deflated so as to insert the balloon into the lumen, the inner circumferential portion dilates. Accordingly, the members inserted into the lumen together with the balloon can be easily mounted on the balloon through the inner circumferential portion.

When the outer circumferential portion is formed of an elastic material, the outer circumferential portion keeps dilating as the internal pressure of the balloon increases. Accordingly, a greater force can be applied to a subject pressed by the balloon.

When the support portions possess a plurality of divided segments that is divided in the axial direction orthogonal to the radial direction, when the balloon is bent, the support portions are smoothly bent as well in response to the bending of the balloon. Accordingly, it is easy to insert the balloon into a bent site in a body cavity.

When the support portions are formed of a sponge, the deflation properties of the support portions become excellent. Accordingly, the deflation of the outer circumferential portion is not easily hindered by the support portions.

When three or more of the first compression portions and three or more of the second compression portions are formed in the circumferential direction at equal intervals, at the time of pressure reduction, the uniform arrangement or the first and second compression portions makes it easy for the entirety of the balloon to uniformly deflate in the circumferential direction. Accordingly, the interference between the balloon and the lumen is more effectively inhibited.

Another aspect of the disclosure here involves a balloon comprising an outer tubular member possessing an interior, expandable from a non-circular cross-section to a circular cross-section upon introducing fluid into the interior of the outer tubular member, and contractable from the circular cross-section upon withdrawing fluid from the interior of the outer tubular member, the outer tubular member possessing an inner surface, the outer tubular member possessing a center and a maximum outer diameter portion farthest from the center in a radially outward direction. The balloon further comprises an inner tubular member inside the outer tubular member, the inner tubular member possessing an outer surface, a plurality of circumferentially spaced apart compressible first compression portions positioned between the outer surface of the inner tubular member and the inner surface of the outer tubular member, and a plurality of circumferentially spaced apart compressible second compression portions positioned between the outer surface of the inner tubular member and the inner surface of the outer tubular member. Each one of the second compression portions is located circumferentially between circumferentially adjacent pairs of the first compression portions. Each of the first compression portions is more compressible than the plurality of the second compression portions. A minimum expanding pressure is defined as the lowest pressure of the fluid in the interior of the outer tubular member necessary to expand the outer tubular member from the non-circular cross-section to the circular cross-section. When the outer tubular member contracts to compress the first compression portions and the second compression portions, a distance between the center of the outer tubular member and the maximum outer diameter portion of the tubular member is less than a radius of the circular cross-section of the outer tubular member when the minimum expanding pressure is applied to the outer tubular member.

Another aspect of the disclosure here involves a method of treating a treatment site. The method comprises: inserting a balloon into a body, the balloon possessing an outer surface, an interior, a maximum outer diameter portion and a non-circular cross-section; moving the balloon in the body to a treatment site in the body; outwardly expanding the balloon located at the treatment site in the body by introducing a minimum expansion pressure into the interior of the balloon, the minimum expansion pressure being a minimum pressure necessary to expand the balloon from possessing the non-circular cross-section to possess a circular cross-section with a radius, and outwardly expanding the balloon further by increasing the interior pressure, thereby pressing the outer surface of the balloon into contact with the treatment site; contracting the balloon so that a distance from the center of the of the balloon to the maximum outer diameter portion is always less than the radius of the balloon when the minimum expansion pressure is applied to the interior of the balloon; and removing the balloon from the body while the balloon is in the contracted position.

DETAILED DESCRIPTION

Hereinafter, the embodiments of the balloon, representing examples of the invention disclosed here, will be described with reference to drawings. For facilitating understanding, the dimensional ratios of the drawings are magnified and may differ from the actual ratios.

The term "dilate" as used throughout this specification means "expand". The term "deflate" as used throughout this specification means "contract."

Figure 1:
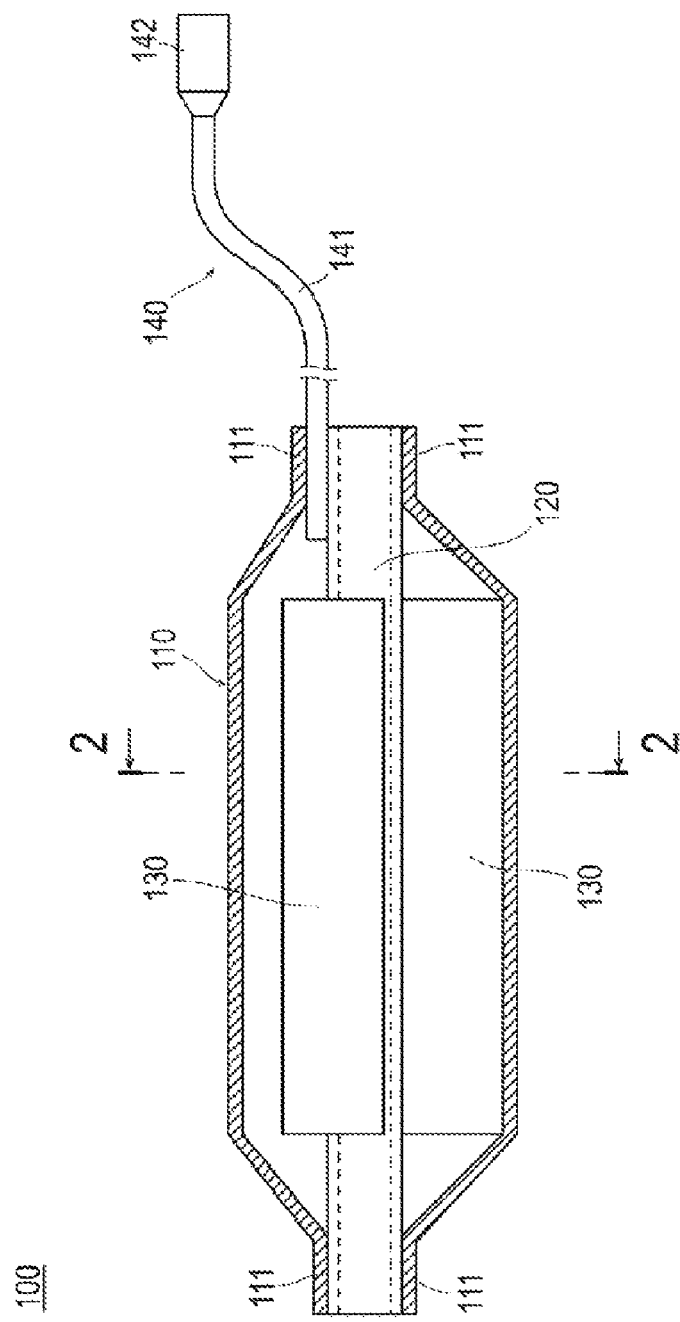
FIG. 1 is a view schematically showing the constitution of a balloon of a first embodiment.

As shown in FIG. 1, a balloon 100 of the first embodiment has an outer circumferential portion 110, an inner circumferential portion 120, support portions 130, and a fluid supply and drainage portion 140.

The outer circumferential portion 110 is a tubular member, has a cylindrical shape and is flexible. The outer circumferential portion 110 is formed of an elastic material. Examples of the material forming the outer circumferential portion 110 include polymers such as silicone rubber, latex rubber, polyolefin, crosslinked polyolefin, polyvinyl chloride, polyamide, a polyamide elastomer, polyester, a polyester elastomer, a polystyrene elastomer, polyurethane, a polyurethane elastomer, a fluororesin, polyimide, and the like, and a mixture including any of these. Examples of the polyolefin include polyethylene, polypropylene, polybutene, an ethylene-propylene copolymer, an ethylene-vinyl acetate copolymer, an ionomer, and a mixture composed of two or more kinds of these.

An end portion 111 of the outer circumferential portion 110 is integrally formed with the inner circumferential portion 120. The space between the end portion 111 and the inner circumferential portion 120 is airtight.

The inner circumferential portion 120 is a tubular member, has a cylindrical shape and is flexible. The inner circumferential portion 120 is formed of an elastic material. The inner circumferential portion 120 and the outer circumferential portion 110 may be formed of the same material.

Figure 2:
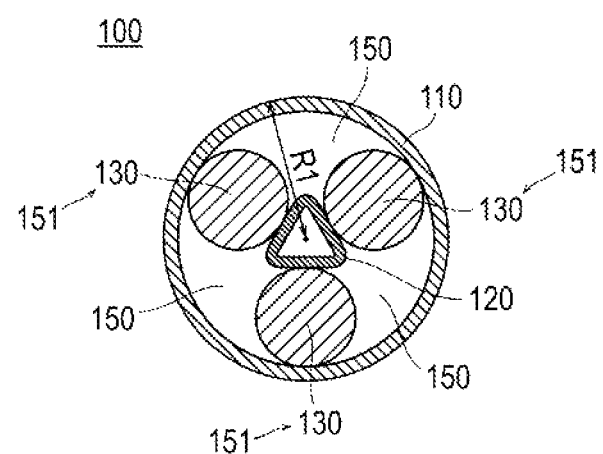
FIG. 2 is a cross-sectional view taken along line II-II of FIG. 1, showing the dilated balloon of the first embodiment.
Figure 3:
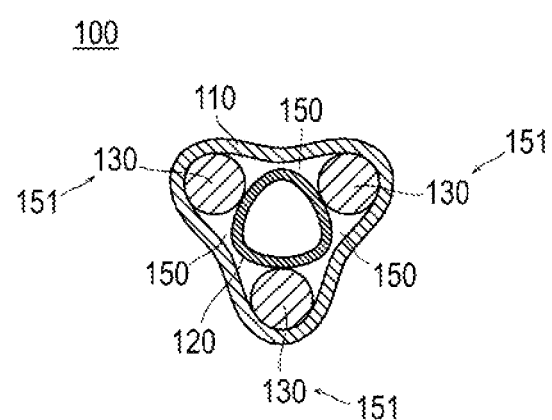
FIG. 3 is a cross-sectional view of the balloon of the first embodiment that has deflated due to pressure reduction.
Figure 4:
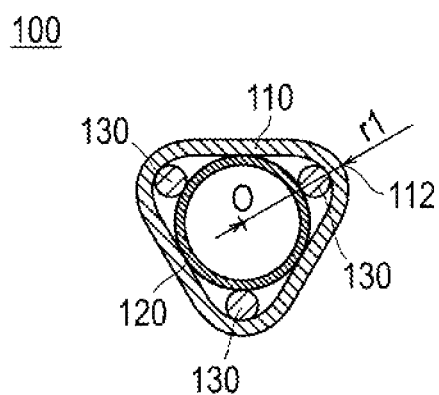
FIG. 4 is a cross-sectional view of the balloon of the first embodiment that has deflated due to further reduction in pressure.

The support portions 130 have a solid columnar shape (i.e., in the shape of a column that is not hollow, as shown in FIGS. 2-4), and are disposed in the form of a straight line along the inner circumferential portion 120 (i.e., the support portions 130 extend parallel to the inner circumferential portion 120). The support portions 130 are formed of a sponge. For example, the sponge may be an open cell-type foam structure in which foams (i.e., compressible volumes) are formed on the surface and inside of the sponge, but the sponge is not limited to this structure. The material forming the support portions 130 is not limited to those enumerated, but examples include various elastomers such as urethane, polyethylene, EPDM, and the like.

The fluid supply and drainage portion 140 has a tube 141 and a connector 142.

The tube 141 is flexible. The distal end of the tube 141 extends into the space between the end portion 111 of the outer circumferential portion 110 and the inner circumferential portion 120. The tube 141 is in communication with the space formed between the outer circumferential portion 110 and the inner circumferential portion 120.

The connector 142 is mounted on the proximal end of the tube 141 and connected to, for example, a pressure regulator such as a syringe or the like. When an actuating fluid is supplied into the balloon from the pressure regulator through the tube 141, the internal pressure of the space between the outer circumferential portion 110 and the inner circumferential portion 120 increases. When the actuating fluid is discharged to the pressure regulator through the tube 141, the internal pressure of the space between the outer circumferential portion 110 and the inner circumferential portion 120 is reduced. For example, the actuating fluid is a gas such as air or the like or a liquid such as distilled water, physiological salt solution or the like.

As shown in FIG. 2, the dilated outer circumferential portion 110 has a hollow circular cross-section. The inner circumferential portion 120 is provided inside the hollow circular cross-section of the outer circumferential portion 110.

The support portions 130 are interposed between the outer circumferential portion 110 and the inner circumferential portion 120. The support portions 130 are attached to the inner surface of the outer circumferential portion 110 and support the outer circumferential portion 110 while separating or spacing the outer circumferential portion 110 from the inner circumferential portion 120. The support portions 130 press the inner circumferential portion 120 in the radially inward direction, and support the inner circumferential portion 120 such that the inner circumferential portion 120 is positioned approximately at the center of the circular cross-section of the outer circumferential portion 110.

A plurality of support portions 130, circumferentially separated or spaced apart from each other, are arranged in the circumferential direction. As a result, the support portions 130 form a plurality of relatively high compression portions (first compression portions) 150, which have a relatively high compressive strain (i.e., are relatively highly compressible), and a plurality of relatively low compression portions (second compression portions) 151, which have a relatively low compressive strain (i.e., are relatively low in compressibility and are less compressible than the high compression portions), in the circumferential direction. Each of the relatively high compression portions 150 is a space between the support portions 130. The relatively low compression portions 151 are composed of the support portions 130. Three of the relatively high compression portions 150 are formed in the circumferential direction at equal intervals, and three of the relatively low compression portions 151 are formed in the circumferential direction at equal intervals.

The outer circumferential portion 110 is formed of an elastic material. Consequently, as the internal pressure of the outer circumferential portion 110 increases, the outer circumferential portion 110 dilates toward the outside of the balloon in the radial outward direction in the form of a concentric circle. In a state in which no external force, other than the atmospheric pressure, is applied to the balloon 100, the minimum pressure, which is the lowest pressure necessary for dilating the deflated outer circumferential portion 110 and making the outer circumferential portion 110 have or possess a circular cross-section (hereinafter, the minimum pressure described above is simply referred to as the minimum dilating pressure), is 0.75 atm to 1.5 atm, for example. When the outer circumferential portion 110 dilates in the radially outward direction so that the outer circumferential portion 110 possesses a concentric circular cross-section, the inner circumferential portion 120 is compressed to possess a triangular cross-section.

The outer circumferential portion 110 keeps dilating as the internal pressure increases. At this time, the support portions 130 are interposed between the outer circumferential portion 110 and the inner circumferential portion 120, and therefore positional deviation (i.e., a change in position) of the support portions 130 does not occur. The support portions 130 may be bonded to at least one of the outer circumferential portion 110 and the inner circumferential portion 120.

As shown in FIG. 3, when the internal pressure of the outer circumferential portion 110 is reduced and becomes smaller than the minimum dilating pressure, the outer circumferential portion 110 deflates while compressing the relatively high compression portions 150 and the relatively low compression portions 151. At this time, nothing supports the outer circumferential portion 110 in the relatively high compression portions 150, and therefore the relatively high compression portions 150 cave in toward the inside (i.e., the relatively high compression portions 150 contract or move radially inward).

When the internal pressure of the space between the inner circumferential portion 120 and the outer circumferential portion 110 is reduced and becomes less than the minimum dilating pressure, and the force applied toward the inside in the radial direction weakens, the inner circumferential portion 120 dilates toward the outside in the radial direction.

When the gas or liquid contained in the sponge, which is a material constituting the support portions 130, escapes due to pressure reduction, the support portions 130 deflate, and the diameter of the support portions 130 is reduced. Furthermore, the support portions 130 are compressed by the deflating outer circumferential portion 110 and the dilating inner circumferential portion 120. The support portions 130 support the deflating of the outer circumferential portion 110.

As shown in FIG. 4, when the internal pressure of the outer circumferential portion 110 is further reduced, the deflated outer circumferential portion 110 comes into contact with the dilated inner circumferential portion 120. The dilated inner circumferential portion 120 has a circular cross-section at this time, and as a result, most of the space constituting the relatively high compression portions 150 is deflated, and the diameter of the support portions 130 is further reduced.

At this time, a distance r1 between the origin, which is a center O of the circular cross-section of the dilated outer circumferential portion 110, and a maximum outer diameter portion 112 that protrudes the most toward the outside in the radial direction is shorter than a radius R1 of the outer circumferential portion 110 that is obtained when the minimum dilating pressure is applied toward the inside (r1<R1).

Next, a treatment that is provided to the stenosed site of the lumen by using the balloon 100 will be described by illustrating urethral stricture as an example.

Figure 5:
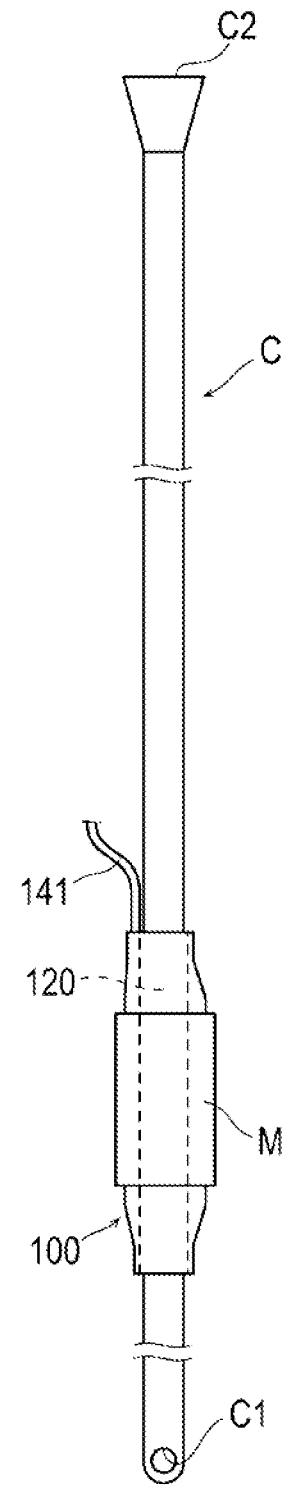
FIG. 5 is a view showing the balloon of the first embodiment mounted on a urinary catheter.

As shown in FIG. 5, the balloon 100 may be used together with a urinary catheter C.

The urinary catheter C has a tubular shape and is formed of a flexible material. In the urinary catheter C, an opening portion C1 is formed in the outer circumferential portion in the vicinity of the distal end of the urinary catheter C. Furthermore, an opening portion is also formed at a proximal end C2 of the urinary catheter C. The opening portion C1 is in communication with both the inside of the urinary catheter C and the opening portion of the proximal end C2. Other devices known in the related art can be used as the urinary catheter C.

The urinary catheter C is mounted on the balloon 100 through the inner circumferential portion 120. At this time, the balloon 100 stays deflated. While the balloon 100 is deflated, the inner circumferential portion 120 is dilated. Accordingly, the urinary catheter C can easily pass through the inner circumferential portion 120.

In the outer circumferential portion of the balloon 100, a medical material M providing, for example, an epithelial function is disposed. The medical material M is a sheet in the shape of a cylinder. The medical material M is obtained by processing the epithelium collected from a living body. The epithelium may be collected from any sites in the living body. However, the epithelium is preferably oral mucosa. The oral mucosa contains epithelial cells.

Figure 6:
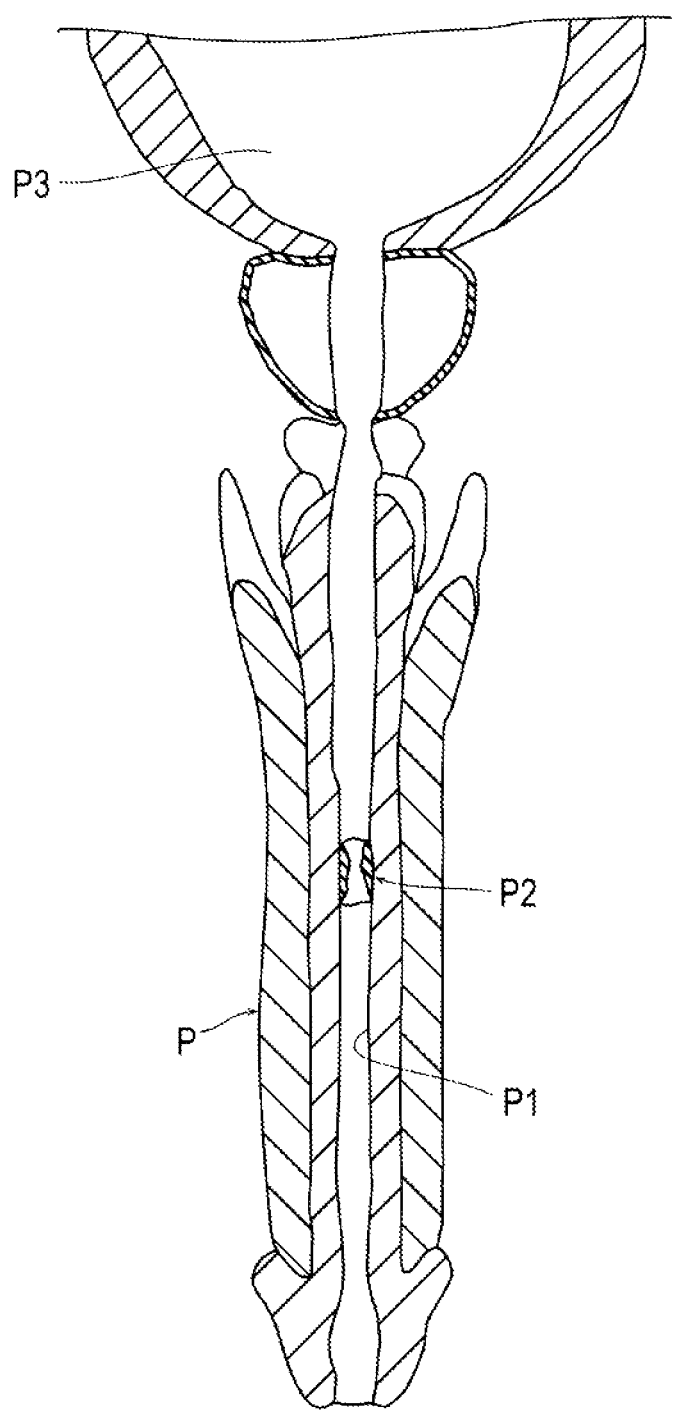
FIG. 6 is a cross-sectional view showing the urethra, in which a stenosed site is formed, and the bladder.

As shown in FIG. 6, urethral stricture is a disease caused when a stenosed site P2 is formed in urethra P1 in penis P due to a scar tissue. In the process in which the mucosa of the urethra P1 is damaged and then healed, the mucosa of the urethra P1 or the corpus spongiosum penis surrounding the mucosa of the urethra P1 undergoes cicatrization, and as a result, scar tissue is formed.

To treat the urethral stricture, an operator first inserts an endoscope into the urethra P1. By using the endoscope, the operator provides a treatment such as incision, cutting, excision, or the like to the stenosed site P2. After the treatment, the operator removes the endoscope.

Figure 7:
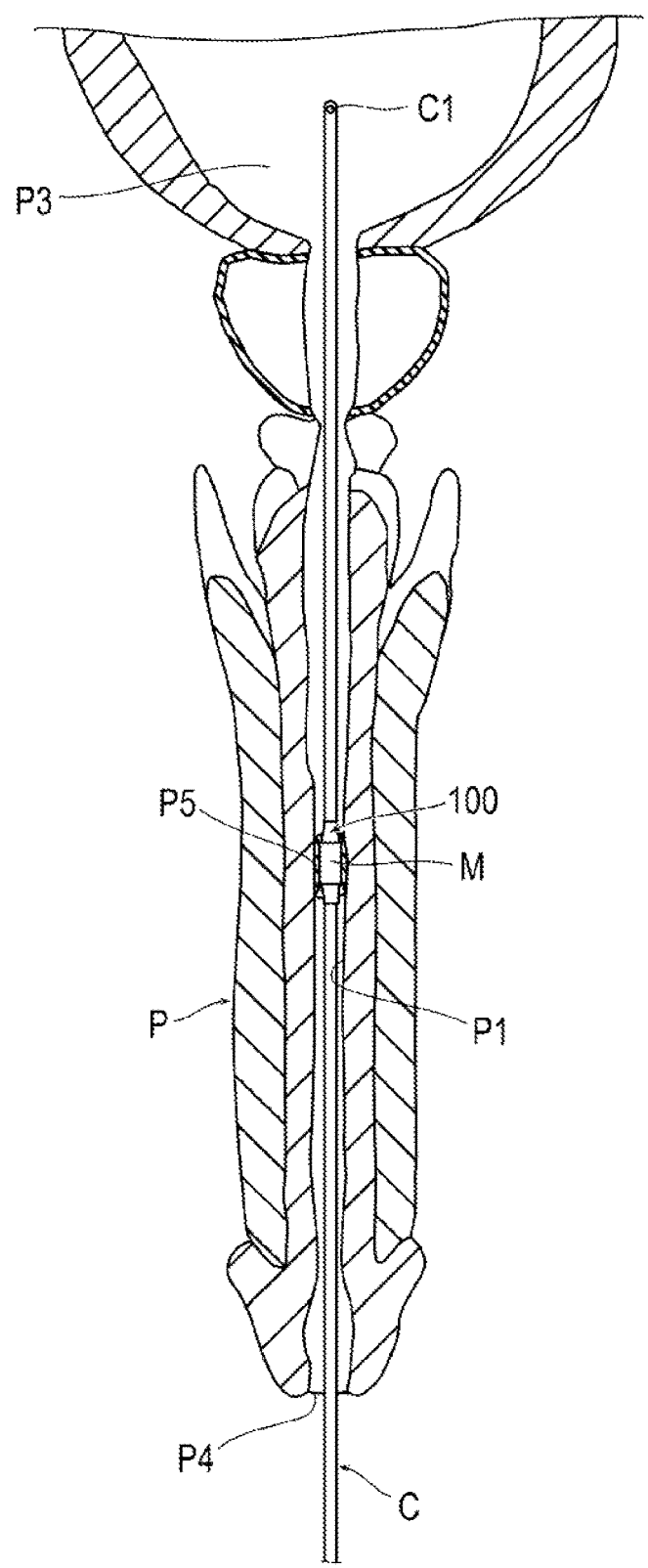
FIG. 7 is a view showing the balloon, together with the urinary catheter, inserted into the urethra.

Thereafter, as shown in FIG. 7, the operator inserts the balloon 100 into the urethra P1 together with the urinary catheter C from external urethral orifice P4. The balloon 100 is disposed in a treatment site P5. The treatment site P5 is a site from which the scar tissue has been removed as a result of the aforementioned treatment such as incision or the like provided to the stenosed site P2. The opening portion C1 at the distal end of the urinary catheter C is disposed inside bladder P3. The urine retained in the bladder P3 is discharged toward the proximal side of the urinary catheter C through the opening portion C1.

After the opening portion C1 is disposed in the bladder P3, and the balloon 100 is disposed in the treatment site P5, the operator dilates the balloon 100. The tube 141 shown in FIGS. 1 and 2 that is in communication with the inside of the balloon 100 is led outside the body from the external urethral orifice P4, although this is not shown in FIG. 7 for clarity.

When the balloon 100 dilates, the medical material M is pressed and bonded onto the treatment site P5. The exposure of the treatment site P5 to liquid such as urine or the like is not preferable because the scar tissue may become thick, and the urethral stricture may reoccur. If the medical material M is pressed and bonded onto the treatment site P5, the epithelial cells are reconstructed in or engrafted into the treatment site P5. As a result, the epithelial function is provided to the treatment site P5 (the treatment site P5 obtains the epithelial function). Specifically, the epithelial function includes a function of protecting the treatment site P5 from liquid (urine or an inflammatory component), other internal secretions of a living body, various germs, and the like.

After pressing and bonding the medical material M onto the treatment site P5, the operator deflates the balloon 100 and removes it from the urethra P1 together with the urinary catheter C.

Next, the operation and effect of the present embodiment will be described.

If a balloon does not have the support portions 130 (i.e., unlike the balloon 100 of the present embodiment), when the internal pressure of the outer circumferential unit 110 is reduced, the outer circumferential portion 110 is crushed and flattened such that the inner circumferential portion 120 is stuck or lodged in the outer circumferential unit 110. The deflated and flattened outer circumferential portion 110 has an oval cross-sectional shape. In the direction of the minor axis of this oval cross-section, the outer circumferential portion 110 deflates toward the inside in the radial direction. However, in the direction of the major axis of the oval cross-section, the outer circumferential portion 110 protrudes toward the outside in the radial direction without deflating, and the outer diameter becomes greater than the radius R1 obtained when the minimum dilating pressure is applied. Consequently, the protruding portion interferes with the urethra P1 (hindering removal of the balloon 100).

In contrast, in the present embodiment, the outer circumferential portion 110 deflates while compressing the relatively high compression portions 150 and the relatively low compression portions 151. As a result, the entirety of the outer circumferential portion 110 deflates in the circumferential direction without being crushed and flattened as described above. Furthermore, in the maximum outer diameter portion 112, the distance r1 from the center O becomes shorter than the radius R1 obtained when the minimum dilating pressure is applied (r1<R1).

In this way, the balloon 100 deflates such that the overall size in the circumferential direction is always smaller than the size of the balloon which dilates to have a circular cross-section obtained when the minimum dilating pressure is applied. Accordingly, the balloon 100 does not interfere with the urethra P1 and can be easily removed.

Furthermore, in the balloon 100 of the present embodiment, the relatively high compression portions 150 and the low compression portions 151 are not concentrated in a certain position. Three of the relatively high compression portions 150 and three of the low compression portions 151 are provided in the circumferential direction at equal intervals. Accordingly, at the time of pressure reduction, the entirety of the outer circumferential portion 110 relatively uniformly deflates in the circumferential direction and does not have a site that significantly protrudes. Therefore, the interference between the balloon 100 and the urethra P1 is very effectively inhibited (i.e., there is minimal or no interference for removal of the balloon).

In the balloon 100, the force of fastening the urinary catheter C to the balloon through the inner circumferential portion 120 is changed as the inner circumferential portion 120 dilates or deflates. Therefore, the holding force applied to the urinary catheter C can be regulated. If the holding force is weakened by dilating the inner circumferential portion 120, the position of the urinary catheter C and the position of the balloon 100 are easily adjusted relative to each other, and the urinary catheter C can be easily attached to or detached from the balloon 100. When the urinary catheter C and the balloon 100 indwell in an intended position in the urethra P1, if the holding force is increased by deflating the inner circumferential portion 120, the positional deviation (i.e., change in position) of the urinary catheter C is prevented.

The outer circumferential portion 110 in the balloon 100 is an elastic material. Therefore, the balloon 100 dilates as the internal pressure increases. Accordingly, the balloon 100 applies a strong force to the medical material M. When a stronger force is applied to the medical material M from the balloon 100, and thus the medical material M is pressed more firmly onto the treatment site P5, the medical material M is more uniformly pressed and bonded onto the treatment site P5.

The support portions 130 in the balloon 100 are formed of a sponge, and the deflation properties of the support portions 130 are excellent (i.e., the support portions 130 are compressible). Accordingly, the deflation of the outer circumferential portion 110 is not easily hindered by the support portions 130.

Figure 8:
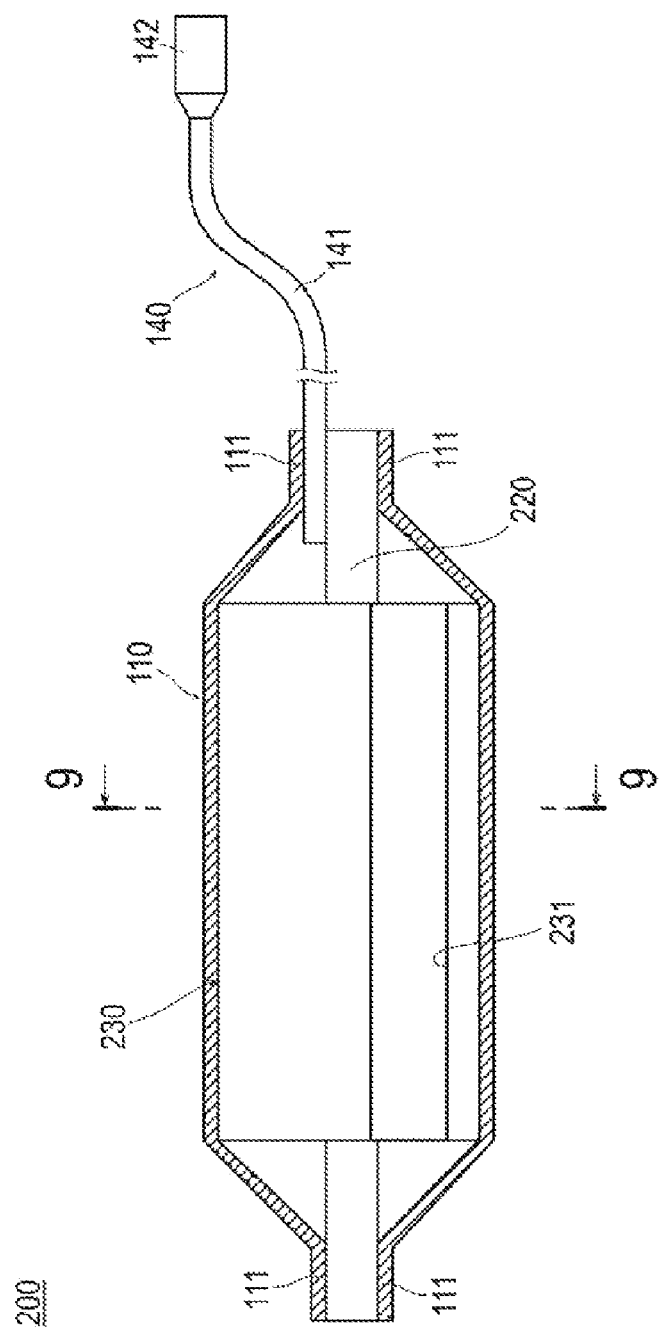
FIG. 8 is a view schematically showing the constitution of a balloon of a second embodiment.

As shown in FIG. 8, a balloon 200 of the second embodiment has a support portion 230 and an inner circumferential portion 220 that are different from the support portions 130 and the inner circumferential portion 120 of the first embodiment. Other components and the method of use are the same for the balloon 200 and the balloon 100 of the first embodiment. In FIG. 8, the components common to the balloons 100 and 200 are marked with the same reference numerals.

Figure 9:
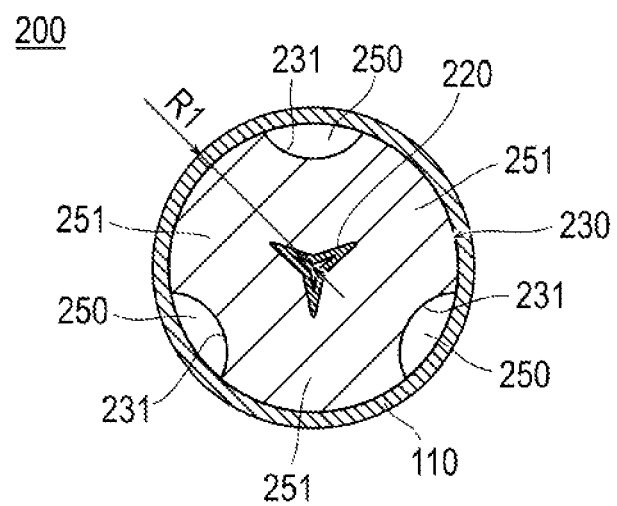
FIG. 9 is a cross-sectional view taken along line IX-IX of FIG. 8, showing the dilated balloon of the second embodiment.

As shown in FIG. 9, the support portion 230 within the outer circumferential surface expands outwardly in the circumferential direction to come into surface contact with the outer circumferential portion 110. Furthermore, external grooves 231 are formed on the outer circumferential surface. As shown in FIG. 8, the grooves 231 extend in the axial direction. The support portion 230 is formed of a sponge. The support portion 230 has an open cell-type foam structure similar to the support portions 130 of the first embodiment, and is formed of the same material as the material of the support portions 130. However, the foam structure and the material forming the support portion 230 are not limited to this structure or these materials.

The grooves 231 form relatively high compression portions (first compression portions) 250, which have a relatively high compressive strain, between the support portion 230 and the outer circumferential portion 110. The portions of the support portion 230 between the grooves 231 form relatively low compression portions (second compression portions) 251 which have a relatively low compressive strain (i.e., are relatively low in compressibility and are less compressible than the relatively high compression portions). Three of the relatively high compression portions 250 are formed in the circumferential direction at equal intervals, and three of the low compression portions 251 are formed in the circumferential direction at equal intervals.

As shown in FIG. 9, the deflated inner circumferential portion 220 has a cross-sectional shape that is different from the triangular cross-sectional shape of the inner circumferential portion 120 of the first embodiment. However, the material, the function, and the like of the inner circumferential portion 220 are the same as those of the inner circumferential portion 120 of the first embodiment.

Figure 10:
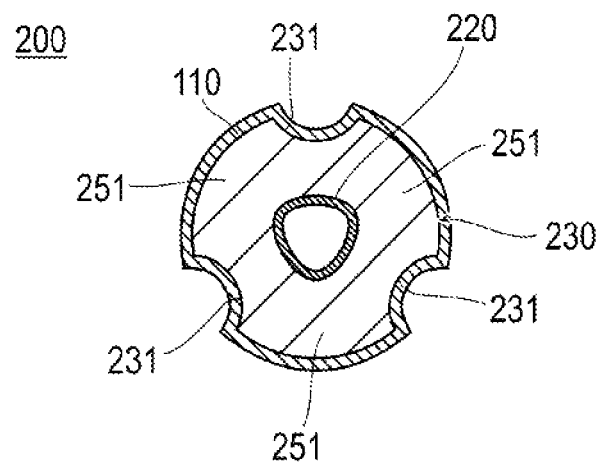
FIG. 10 is a cross-sectional view of the balloon of the second embodiment that has deflated due to pressure reduction.

As shown in FIG. 10, when the internal pressure of the outer circumferential unit 110 is reduced and becomes smaller than the minimum dilating pressure, the outer circumferential portion 110 is deformed to come into close contact with the grooves 231. In this way, the outer circumferential portion 110 deflates while compressing the relatively high compression portions 250 and the relatively low compression portions 251.

When the internal pressure of the space between the outer circumferential portion 110 and the inner circumferential portion 220 is reduced and becomes smaller than the minimum dilating pressure, and the force applied toward the inside of the balloon in the radial direction is weakened, the inner circumferential portion 220 dilates toward the outside of the balloon in the radial direction.

When the gas or liquid contained in the sponge, which is the material constituting the support portion 230, escapes due to pressure reduction, the support portion 230 deflates by itself and is compressed by the deflating outer circumferential portion 110 and the dilating inner circumferential portion 220. The support portion 230 supports the deflating outer circumferential portion 110 while being compressed.

Figure 11:
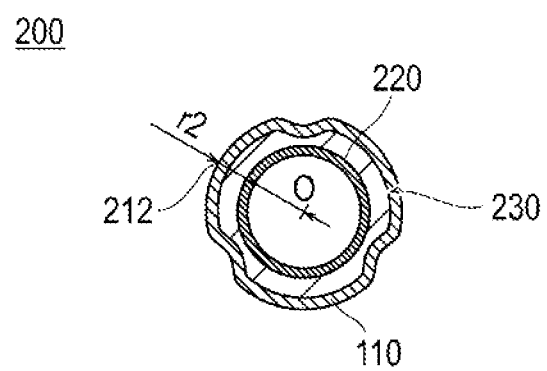
FIG. 11 is a cross-sectional view of the balloon of the second embodiment that has deflated due to further reduction in pressure.

As shown in FIG. 11, when the pressure is further reduced, the support portion 230 is further compressed between the deflated outer circumferential portion 110 and the inner circumferential portion 220 that has a circular cross-section as a result of dilation.

At this time, a distance r2 between an origin, which is the center O of the circular cross-section of the dilated outer circumferential portion 110, and a maximum outer diameter portion 212 that protrudes most toward the outside of the balloon in the radial direction is shorter than the radius R1 of the circular cross-section of the outer circumferential portion 110 that is formed when the minimum dilating pressure is applied toward the inside of the balloon (r2<R1).

In the balloon 200 of the present embodiment, the shape of the inner circumferential portion 220 and the support portion 230 is different from that of the inner circumferential portion 120 and the support portions 130 of the first embodiment. However, the inner circumferential portion 220 and the support portion 230 function similar to the inner circumferential portion 120 and the support portions 130 of the first embodiment. Furthermore, the components other than the inner circumferential portion 220 and the support portion 230 are the same for the balloon 200 of the present embodiment and the balloon 100 of the first embodiment. Therefore, the balloon 200 of the present embodiment can bring about the same operation and effect as those of the balloon 100 of the first embodiment.

In the second embodiment, the support portion 230 comes into surface contact with the outer circumferential portion 110 within the outer circumferential surface expanding in the circumferential direction, and therefore the outer circumferential portion 110 is supported over a wide region by the support portion 230 (i.e., there is a relatively large contact area between the inner face of the outer circumferential portion and the outer face of the support portion 230). Accordingly, when the balloon 200 dilates and indwells the treatment site P5 of the urethra P, the medical material M is more uniformly applied to the treatment site P5.

Figure 12:
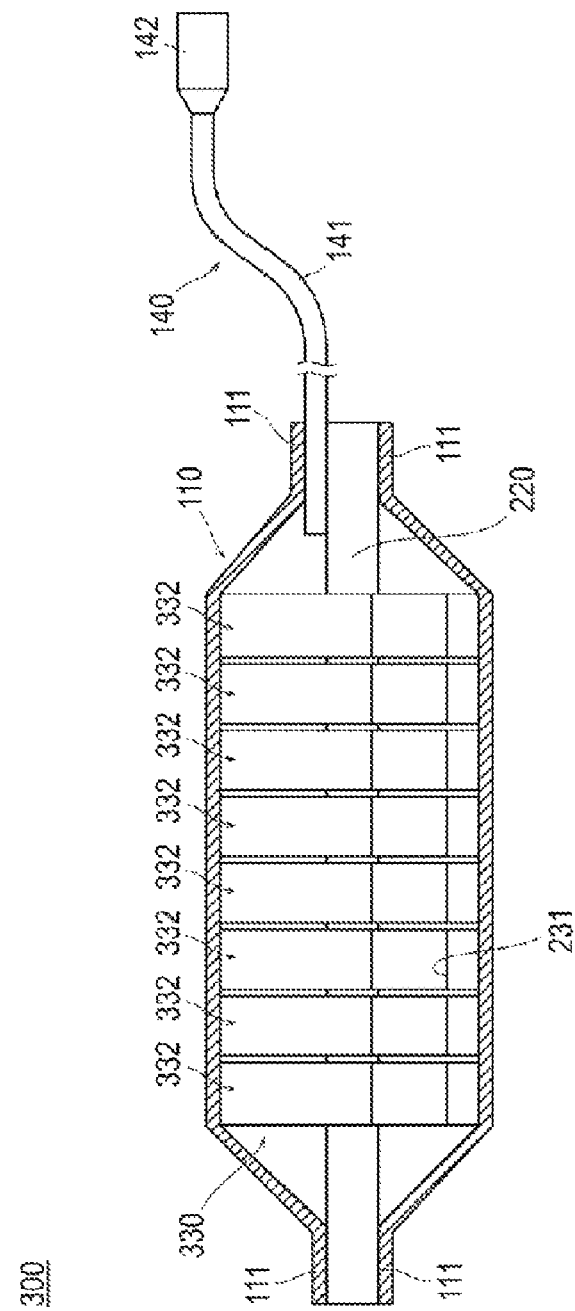
FIG. 12 is a view schematically showing the constitution of a balloon of a third embodiment.

As shown in FIG. 12, a balloon 300 of the third embodiment is different from the balloon 200 of the second embodiment in that a support portion 330 is divided in the axial direction orthogonal to the radial direction. Other components are the same for the balloon 300 and the balloon 200 of the second embodiment. In FIG. 12, the components common to the balloons 200 and 300 are marked with the same reference numerals.

The support portion 330 possesses a plurality of divided segments 332 that are divided and align in the axial direction. The divided segments 332 are formed of a sponge. At the time of dilation, the divided segments 332 have the same cross-sectional shape as that of the support portion 230 of the second embodiment shown in FIG. 9. Furthermore, at the time of pressure reduction, the divided segments 332 are deformed in the same manner as the support portion 230 shown in FIGS. 10 and 11.

Figure 13:
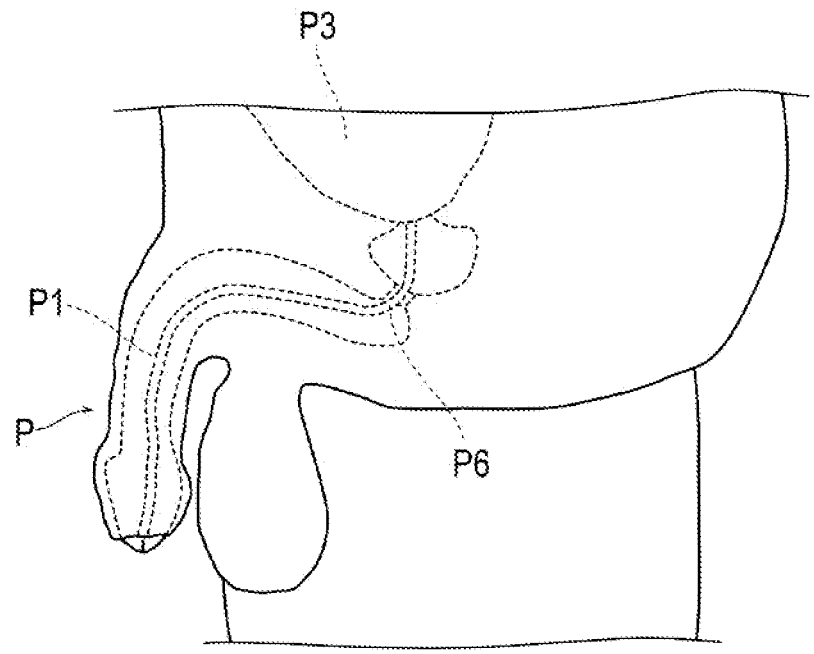
FIG. 13 is a view showing bent sites of the urethra.

In the present embodiment, the support portion 330 has the divided segments 332 that are divided in the axial direction. Accordingly, when the balloon 300 is bent, the support portion 330 is smoothly bent in response to the bending of the balloon 300. Consequently, it is easy to insert the balloon 300 into a bent site P6 in the urethra P1 shown in FIG. 13.

Figure 14:
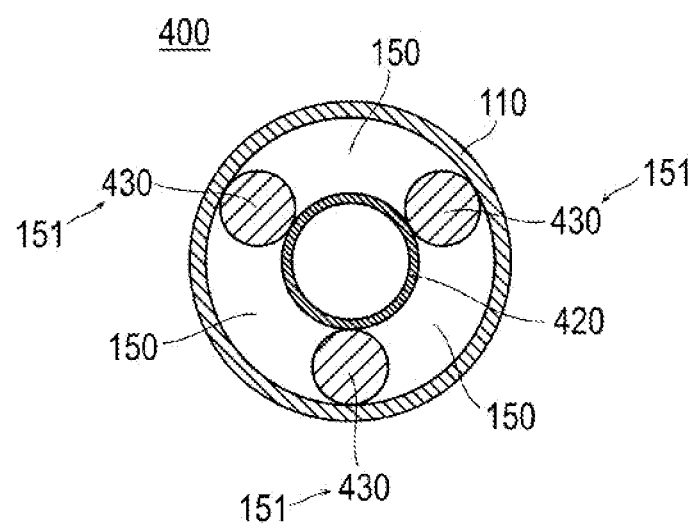
FIG. 14 is a cross-sectional view of a dilated balloon of a fourth embodiment.

As shown in FIG. 14, a balloon 400 of the fourth embodiment has an inner circumferential portion 420 and support portions 430 that are different from those of the first embodiment. Other components are the same for the balloon 400 and the balloon 100 of the first embodiment. In FIG. 14, the components common to the balloons 400 and 100 are marked with the same reference numerals.

The inner circumferential portion 420 does not dilate or deflate as the pressure between the outer circumferential portion 110 and the inner circumferential portion 420 increases or decreases. The diameter of the inner circumferential portion 420 is constant (i.e., does not change) regardless of the pressure between the outer circumferential portion 110 and the inner circumferential portion 420. Examples of the material forming the inner circumferential portion 420 include polyolefin such as polyethylene, polypropylene, an ethylene-propylene copolymer, and the like, polyester such as polyethylene terephthalate and the like, a thermoplastic resin such as polyvinyl chloride, an ethylene-vinyl acetate copolymer, a crosslinkable ethylene-vinyl acetate copolymer, polyurethane, and the like, a polyamide elastomer, a polystyrene elastomer, silicone rubber, latex rubber, and the like.

The diameter of the support portion 430 is different from that of the support portions 130 of the first embodiment. Except for the diameter, the supports portions 430 are the same as the support portions 130 of the first embodiment.

Figure 15:
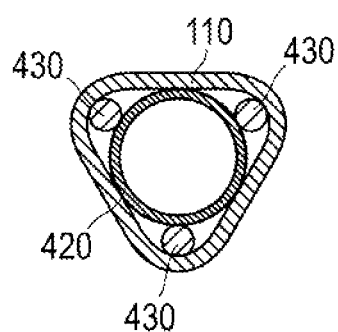
FIG. 15 is a cross-sectional view of the balloon of the fourth embodiment that has deflated due to pressure reduction.

As shown in FIG. 15, at the time of pressure reduction, the outer circumferential portion 110 and the support portions 430 deflate in the same manner as in the first embodiment. At this time, the diameter of the inner circumferential portion 420 does not change from the diameter before pressure reduction.

In the fourth embodiment, the inner circumferential portion 420 does not dilate or deflate. However, the components other than the inner circumferential portion 420 bring about the same operation and effect as those of the first embodiment.

The balloon disclosed here is not limited to the aforementioned embodiments, and can be modified in various ways within the scope of claims.

Figure 16:
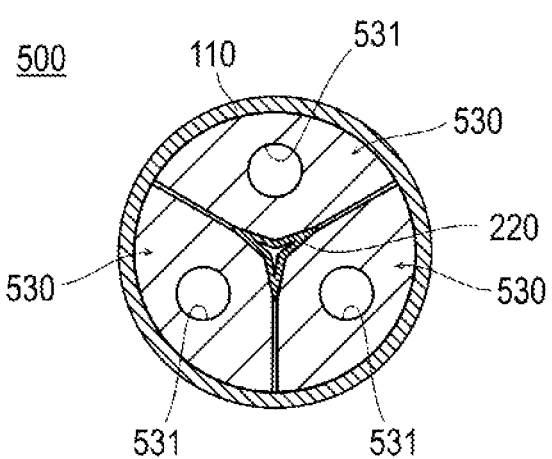
FIG. 16 is a cross-sectional view of a dilated balloon of Modification example 1.
Figure 17:
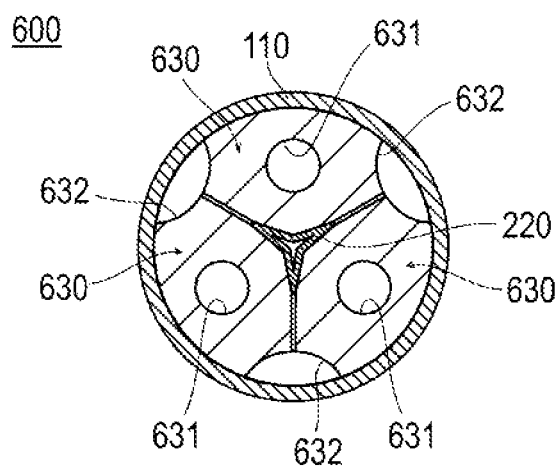
FIG. 17 is a cross-sectional view of a dilated balloon of Modification example 2.

For example, the balloon disclosed here may be modified as shown in FIGS. 16 and 17, by changing the support portion 230 of the second embodiment shown in FIG. 9. Unlike the support portion 230 of the second embodiment, support portions 530 and 630 in these modification examples are divided in the circumferential direction. Except for the support portions 530 and 630 of the modification examples shown in FIGS. 16 and 17, the components of the present modification examples are the same as those of the second embodiment. In FIGS. 16 and 17, the components other than the support portions 530 and 630 are marked with the same reference numerals as those of the second embodiment.

As shown in FIG. 16, holes 531 are formed in the support portions 530. The holes 531 penetrate the support portions 530 in the axial direction. The holes 531 form relatively high compression portions (first compression portions). In the support portions 530, the portions other than the holes 531 form relatively low compression portions (second compression portions).

As shown in FIG. 17, holes 631 are formed in the support portions 630. Furthermore, in the support portions 630, grooves 632 are formed. The holes 631 penetrate the support portions 630 in the axial direction. The grooves 632 extend in the axial direction. The holes 631 and the grooves 632 form relatively high compression portions (first compression portions). In the support portions 630, the portions other than the holes 631 and the grooves 632 form relatively low compression portions (second compression portions).

Similar to the support portion 230 of the second embodiment, within the outer circumferential surface, the support portions 530 and the support portions 630 come into surface contact with the outer circumferential portion 110 over a wide region. Therefore, the support portions 530 and 630 can bring about the same operation and effect as those of the second embodiment.

Figure 18:
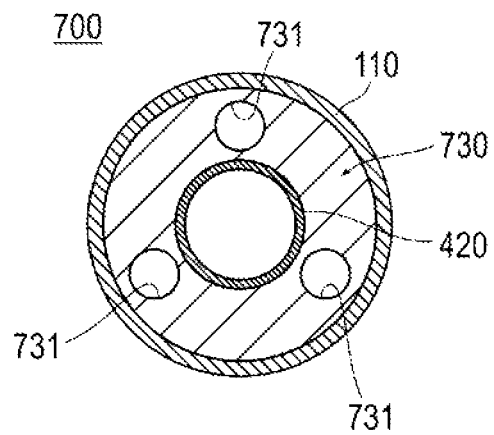
FIG. 18 is a cross-sectional view of a dilated balloon of Modification example 3.
Figure 19:
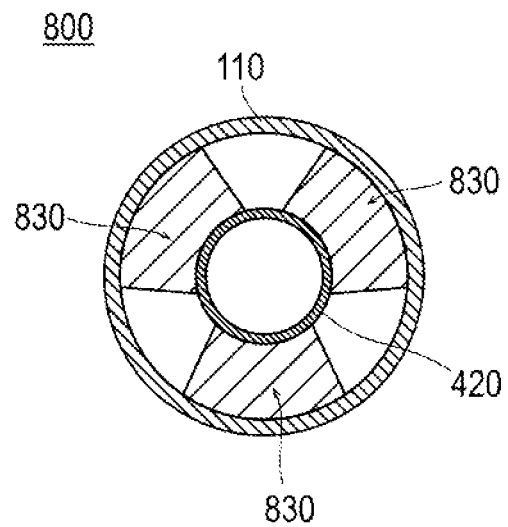
FIG. 19 is a cross-sectional view of a dilated balloon of Modification example 4.

The balloon disclosed here may also be modified as shown in FIGS. 18 and 19 that change the support portions 430 of the fourth embodiment shown in FIG. 14. Both a support portion 730 shown in FIG. 18 and support portions 830 shown in FIG. 19 come into surface contact with the outer circumferential portion 110 within the outer circumferential surface (i.e., the outer surface of each of the support portion 730, 830 contacts the inner surface of the outer circumferential portion 110). Except for the support portions 730 and 830 of the modification examples shown in FIGS. 18 and 19, the components of these modification examples are the same as those of the fourth embodiment. In FIGS. 18 and 19, the components other than the support portions 730 and 830 are marked with the same reference numerals as those of the fourth embodiment.

As shown in FIG. 18, holes 731 are formed in the support portion 730. The holes 731 penetrate the support portion 730 in the axial direction. The holes 731 form relatively high compression portions (first compression portions), and the portions between the holes 731 form relatively low compression portions (second compression portions). As shown in FIG. 19, the support portions 830 are provided in a state of being separated from each other in the circumferential direction. As a result, the relatively high compression portions and the relatively low compression portions are alternately formed.

Figure 20:
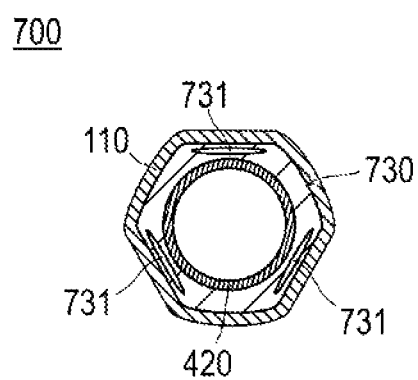
FIG. 20 is a cross-sectional view of the balloon of Modification example 3 that has deflated due to pressure reduction.

As shown in FIG. 20, at the time of pressure reduction, the support portion 730 is compressed such that the holes 731 are crushed.

Figure 21:
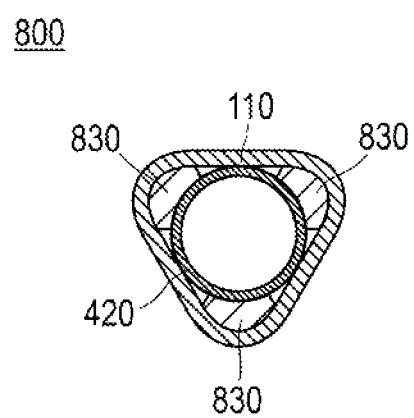
FIG. 21 is a cross-sectional view of the balloon of Modification example 4 that has deflated due to pressure reduction.

As shown in FIG. 21, at the time of pressure reduction, the support portions 830 are compressed by the outer circumferential portion 110, and the relatively high compression portions (first compression portions) between the support portions 830 are crushed by the outer circumferential portion 110.

The support portion 730 and the support portions 830 come into surface contact with the outer circumferential portion 110 within the outer circumferential surface (i.e., the outer face of the support portion 730, 830 contacts the inner surface of the outer circumferential portion 110). In this way, the support portions 730 and 830 support the outer circumferential portion 110 over a wider region compared to the support portions 430 of the fourth embodiment. Therefore, according to these modification examples, in addition to the operation and effect of the fourth embodiment, the operation and effect brought about by the support portion 230 of the second embodiment are also obtained.

Figure 22:
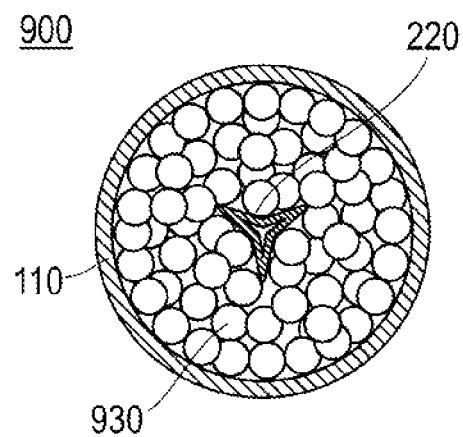
FIG. 22 is a cross-sectional view of a dilated balloon of Modification example 5.

The balloon disclosed here also includes an embodiment of a balloon 900 which has spheres 930 as support portions as shown in FIG. 22. In this case, voids between the spheres 930 become relatively high compression portions (first compression portions), and the spheres 930 become relatively low compression portions (second compression portions). The spheres 930 are formed of, for example, a sponge. Except for the spheres 930, the components of the balloon 900 are the same as those of the second embodiment. In FIG. 22, the components other than the spheres 930 are marked with the same reference numerals as those of the second embodiment.

The medical device disclosed here is not limited to the balloon used for treating the urethral stricture. For example, the disclosure here includes balloons used in a PTA balloon catheter, a tracheostomy tube, gastrostomy, a urinary catheter, a cystostomy catheter, a nephrostomy catheter, a balloon for treating sinusitis, a balloon catheter for stopping gastric variceal bleeding, a balloon for stopping uterine bleeding, various drainage tubes, and the like.

In the aforementioned embodiments and modification examples, the outer circumferential portion has elasticity and keeps dilating as the internal pressure of the balloon increases. However, the present invention is not limited to this embodiment. The balloon disclosed here includes an embodiment in which the outer circumferential portion does not have elasticity and does not dilate even if the internal pressure further increases after it dilates to a predetermined diameter.

In the aforementioned embodiments and modification examples, the relatively high compression portion is composed of a space formed by a hole or a groove or composed of a void formed between members. However, the present invention is not limited to this embodiment. For example, if a hard member (i.e., non-compressible member) is disposed inside the hole 731 shown in FIG. 18, the portion of the hard member has a relatively low compressive strain and thus constitutes a relatively low compression portion, and other portions of the sponge have a relatively high compressive strain and thus constitute a relatively high compression portion. More specifically, if the portion other than the hole 731 in the support portion 730 is formed of an open cell-type sponge that is relatively soft, and a closed cell-type sponge that is relatively hard is provided in the hole 731, the portion of the open cell-type sponge constitutes a relatively high compression portion, and the portion of the closed cell-type sponge constitutes a relatively low compression portion. The closed cell-type sponge has a foam structure in which foams are formed only inside the sponge without being exposed to the surface of the sponge. Furthermore, instead of the closed cell-type sponge, a hard plastic pipe may be provided inside the hole 731.

As described above, the balloon disclosed here includes the embodiment in which relatively high compression portion and the relatively low compression portion are formed by varying the material of the support portion in the circumferential direction.

The balloon disclosed here is not limited to the embodiment in which the relatively high compression portions and the relatively low compression portions are provided in the circumferential direction at equal intervals. The relatively high compression portions and the relatively low compression portions may be provided in the circumferential direction at unequal intervals.

Furthermore, the support portion is not limited to the support portions 130 of the first embodiment shown in FIG. 1 in which the support portions 130 extend in the form of a straight line in the axial direction along the inner circumferential portion. An embodiment may be adopted in which the support portion is twisted so as to be wound around the inner circumferential portion in the form of a helix.

The detailed description above describes examples of a balloon and a treatment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon comprising:
an outer tubular member possessing an interior, expandable from a non-circular cross-section to a circular cross-section upon introducing fluid into the interior of the outer tubular member, and contractable from the circular cross-section upon withdrawing fluid from the interior of the outer tubular member, the outer tubular member possessing an inner surface, the outer tubular member possessing a center and a maximum outer diameter portion farthest from the center in a radially outward direction, the outer tubular member extending in an axial direction;
an inner tubular member inside the outer tubular member, the inner tubular member possessing an outer surface, a distal end and a proximal end, the inner tubular member having an axial extent in the axial direction from the distal end to the proximal end;
a plurality of circumferentially spaced apart compressible first compression portions positioned between the outer surface of the inner tubular member and the inner surface of the outer tubular member, and a plurality of circumferentially spaced apart compressible second compression portions positioned between the outer surface of the inner tubular member and the inner surface of the outer tubular member, each one of the second compression portions being located circumferentially between circumferentially adjacent pairs of the first compression portions;
each of the first compression portions being more compressible than the plurality of the second compression portions;

a minimum expanding pressure being a lowest pressure of the fluid in the interior of the outer tubular member necessary to expand the outer tubular member from the non-circular cross-section to the circular cross-section;

when the outer tubular member contracts to compress the first compression portions and the second compression portions, a distance between the center of the outer tubular member and the maximum outer diameter portion of the tubular member is less than a radius of the circular cross-section of the outer tubular member when the minimum expanding pressure is applied to the outer tubular member;

the inner tubular member possessing a constant cross-section along the axial extent;

the constant cross-section of the inner tubular member being different than the circular cross-section of the outer tubular member when the outer tubular member is expanded; and the constant cross-section of the inner tubular member being different than the non-circular cross-section of the outer tubular member when the outer tubular member is not expanded.

2. The balloon according to claim 1, wherein the inner tubular member is hollow and is configured to expand or contract in the radial direction as the pressure between the outer tubular member and the inner tubular member increases or decreases.

3. The balloon according to claim 1, wherein
the outer tubular member is configured to contract in the radial direction when the pressure between the outer tubular member and the inner tubular member is less than the minimum pressure, and
the inner tubular member possesses a hollow shape and is configured to expand in the radial direction when the pressure between the outer tubular member and the inner tubular member is less than the minimum pressure.

4. The balloon according to claim 1, wherein the first compression portions possess a plurality of divided segments that are divided in an axial direction orthogonal to the radial direction.

5. The balloon according to claim 1, wherein at least three of the first compression portions and at least three of the second compression portions are spaced at equal intervals in the circumferential direction.

6. A balloon comprising:
an outer tubular member possessing an interior, expandable from a non-circular cross-section to a circular cross-section upon introducing fluid into the interior of the outer tubular member, and contractible from the circular cross-section upon withdrawing fluid from the interior of the outer tubular member, the outer tubular member possessing an inner surface, the outer tubular member possessing a center and a maximum outer diameter portion farthest from the center in a radially outward direction, the outer tubular member extending in an axial direction and possessing a circumferential direction;

an inner tubular member inside the outer tubular member, the inner tubular member possessing an outer surface, a distal end and a proximal end;

three circumferentially spaced apart sponges connected to the outer surface of the inner tubular member and positioned between the outer surface of the inner tubular member and the inner surface of the outer tubular member, the three circumferentially spaced apart sponges each extending in the axial direction parallel to the inner tubular member and parallel to the outer tubular member, the three circumferentially spaced apart sponges being equally spaced apart from one another by 120° in the circumferential direction;

three circumferentially spaced apart recesses provided respectively between the three circumferentially spaced apart sponges, the three circumferentially spaced apart recesses being equally spaced apart from one another by 120° in the circumferential direction;

a minimum expanding pressure being a lowest pressure of the fluid in the interior of the outer tubular member necessary to expand the outer tubular member from the non-circular cross-section to the circular cross-section; and when the outer tubular member contracts to compress the three circumferentially spaced apart sponges, a distance between the center of the outer tubular member and the maximum outer diameter portion of the tubular member is less than a radius of the circular cross-section of the outer tubular member when the minimum expanding pressure is applied to the outer tubular member.

7. The balloon according to claim 6, wherein
the inner tubular member possesses an axial extent from the distal end to the proximal end, the inner tubular member having a continuous triangular cross-section along the axial extent of the inner tubular member when the outer tubular member is expanded to have the circular cross-section, and
the inner tubular member possesses a continuous circular cross-section along the axial extent of the inner tubular member when the outer tubular member is contracted.

8. The balloon according to claim 6, wherein the inner tubular member is expandable and contractible along an entirety of the axial extent of the inner tubular member relative to the outer tubular member.

* * * * *